(12) United States Patent
Brown et al.

(10) Patent No.: US 8,139,718 B2
(45) Date of Patent: Mar. 20, 2012

(54) RADIOTHERAPY APPARATUS

(75) Inventors: Kevin Brown, West Sussex (GB); Ralph Streamer, West Sussex (GB); Duncan Bourne, Surrey (GB)

(73) Assignee: Elekta AB (publ), Stockholm (SE)

( * ) Notice: Subject to any disclaimer, the term of this patent is extended or adjusted under 35 U.S.C. 154(b) by 168 days.

(21) Appl. No.: 12/740,291

(22) PCT Filed: Oct. 30, 2007

(86) PCT No.: PCT/EP2007/009404
§ 371 (c)(1),
(2), (4) Date: Apr. 28, 2010

(87) PCT Pub. No.: WO2009/056151
PCT Pub. Date: May 7, 2009

(65) Prior Publication Data
US 2010/0252754 A1    Oct. 7, 2010

(51) Int. Cl.
*G21K 1/04* (2006.01)
*A61N 5/10* (2006.01)

(52) U.S. Cl. ............... 378/147; 378/65; 250/505.1

(58) Field of Classification Search ............ 378/62, 378/65, 147, 151–153, 161, 210; 250/492.23, 250/503.1, 505.1, 526
See application file for complete search history.

(56) References Cited

U.S. PATENT DOCUMENTS
6,052,436 A    4/2000  Huttner et al.
6,459,769 B1   10/2002 Cosman
7,961,843 B2 * 6/2011  Brown et al. ........... 378/65
2004/0034269 A1 * 2/2004 Ozaki ..................... 600/1
2005/0063510 A1  3/2005  Hieronimi et al.
(Continued)

FOREIGN PATENT DOCUMENTS
WO    02069349 A    9/2002
(Continued)

OTHER PUBLICATIONS
International Search Report, Aug. 6, 2008.

*Primary Examiner* — Bernard E Souw
(74) *Attorney, Agent, or Firm* — Westman, Champlin & Kelly, P.A.; Z. Peter Sawicki

(57) ABSTRACT

Realtime beam shape adjustment in response to (for example) online CT scanning of a patient during treatment is assisted by the radiotherapy apparatus comprising a source adapted to emit a beam of therapeutic radiation, a collimator for delimiting the radiation beam, the collimator comprising a plurality of leaves arranged alongside each other and be moveable longitudinally so that the tips of the leaves define a variable edge of the collimator, the leaves being mounted on a support that is moveable laterally with respect to the leaves. In this way, movements of the tumor that are perpendicular to the direction of leaf motion can be accommodated by simply moving the collimator bodily so as to accommodate this. It is preferred that the apparatus also includes a control means adapted to receive information as to the location of the target volume, and, on the basis of that information, control the longitudinal positions of the leaves and the lateral position of the support. It is also preferred that the support tilts as it moves laterally along a path. This can be achieved, by example, by bearings that are moveable on suitable guides, or by mounting the support on a plurality of pivot arms of unequal lengths. The lengths of such pivot arms can be adjusted as necessary.

20 Claims, 3 Drawing Sheets

U.S. PATENT DOCUMENTS

2007/0086569 A1* 4/2007 Johnsen .......................... 378/65
2010/0329422 A1* 12/2010 Brown et al. ................... 378/65
2011/0049396 A1* 3/2011 Furth et al. ................. 250/505.1
2011/0166150 A1* 7/2011 Beato et al. ................... 514/249
2011/0201919 A1* 8/2011 Allen et al. ................... 600/411
2011/0228906 A1* 9/2011 Jaffray et al. .................. 378/65

FOREIGN PATENT DOCUMENTS

WO 2007014026 A 2/2007

* cited by examiner

RADIOTHERAPY APPARATUS

This Application is a Section 371 National Stage Application of International Application No. PCT/EP2007/009404, filed Oct. 30, 2007 and published as WO 2009/056151 A1 on May 7, 2009, the content of which is hereby incorporated by reference in its entirety.

FIELD OF THE INVENTION

The present invention relates to radiotherapy apparatus, and is especially concerned with the control of multi-leaf collimators therefor.

BACKGROUND ART

Radiotherapy apparatus involves the production of a beam of ionising radiation, usually x-rays or a beam of electrons or other sub-atomic particles. This is directed towards a cancerous region of the patient, and adversely affects the tumour cells causing an alleviation of the patient's symptoms. Generally, it is preferred to delimit the radiation beam so that the dose is maximised in the tumour cells and minimised in healthy cells of the patient, as this improves the efficiency of treatment and reduces the side effects suffered by a patient. A variety of methods of doing so have evolved.

One principal component in delimiting the radiation dose is the so-called "multi-leaf collimator" (MLC). This is a collimator which consists of a large number of elongated thin leaves arranged side to side in an array. Each leaf is moveable longitudinally so that its tip can be extended into or withdrawn from the radiation field. The array of leaf tips can thus be positioned so as to define a variable edge to the collimator. All the leaves can be withdrawn to overlap the radiation field, or all the leaves can be extended so as to close it down. Alternatively, some leaves can be withdrawn and some extended so as to define any desired shape, within operational limits. A multi-leaf collimator usually consists of two banks of such arrays, each bank projecting into the radiation field from opposite sides of the collimator.

In addition, radiotherapy apparatus is now often integrated with a diagnostic x-ray source and a two dimensional flat panel detector, that are together able to carry out online CT scanning during treatment of a patient, or immediately before such treatment. Previously, investigative procedures were carried out in order to determine the position of the tumour and then treatment plans were prepared in order to design a dose profile that would apply the desired dose to the tumour cells and a minimum dose to surrounding patient cells. Online CT scanning during treatment allows for the treatment plan to be revised during a treatment, and it has therefore been proposed in principle that there should be feedback from the results of the CT scanning to the control unit setting the MLC leaf positions, so that the radiation beam is delimited to the current actual position of the tumour rather than a previous position at the time when diagnostic procedures were carried out.

SUMMARY OF THE INVENTION

The present invention is based on a realisation that control of the MLC in this way may not be sufficient. In particular, whilst such a link works well in theory, and will work well in practice for movements of tumours that are in the longitudinal direction relative to the leaves (i.e. in the direction of leaf motion) there will be difficulties in accommodating motion in a lateral direction with respect to the leaf, i.e. perpendicular to the direction of leaf motion.

The patent invention therefore provides a radiotherapy apparatus, comprising a source adapted to emit a beam of therapeutic radiation, a collimator for delimiting the radiation beam, the collimator comprising a plurality of leaves arranged alongside each other and be moveable longitudinally so that the tips of the leaves define a variable edge of the collimator, the leaves being mounted on a support that is moveable laterally with respect to the leaves.

In this way, movements of the tumour that are perpendicular to the direction of leaf motion can be accommodated by simply moving the collimator bodily so as to accommodate this. Generally, movements of the tumour during treatments are pure displacements rather than enlargements or reductions of the tumour, and therefore tracking the tumour in this way is likely to be a more efficient manner of accommodating lateral movements than seeking to make appropriate movements of the collimator leaves. In particular, at the lateral edge of a tumour, it is likely that the next adjacent collimator leaf will be fully extended or fully retracted so as to close the radiation field at this point. Thus, if the tumour moves so as to fall into the shadow of a new leaf pair, that leaf pair will need to be suddenly withdrawn or extended to the appropriate position. Likewise, the corresponding leaf pair at the other lateral edge of the tumour will have to be fully closed given that the tumour will no longer be in its shadow.

The movements would have to be very quick, probably in excess of the maximum possible speed of leaf movements. Such speeds are limited by engineering considerations and, in particular, the practicalities of moving very thin very heavy leaves in confined spaces. In the case of an oscillating motion of the tumour, the time required to move the leaves might be greater than the period of oscillation.

It is preferred that the apparatus also includes a control means adapted to receive information as to the location of the target volume, and, on the basis of that information, control the longitudinal positions of the leaves and the lateral position of the support.

It is also preferred that the support is constrained to tilt relative to the lateral motion as it moves along the path. Generally, the leaves within a multi-leaf collimator are not perfectly parallel but are each aimed so that they converge—the point of convergence can be on the source of radiation in order to minimise any penumbra caused by the leaves or (preferably) offset relative to the source so as to minimise leakage between leaves. Thus, it is preferred that the arcuate path is linear, with the tilt allowing the geometry of the leaves to be substantially maintained notwithstanding the lateral movement of the support.

This can be achieved, by example, by bearings that are moveable on suitable guides, or by mounting the support on a plurality of pivot arms of unequal lengths. The lengths of such pivot arms can be adjusted as necessary to provide the appropriate movement.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
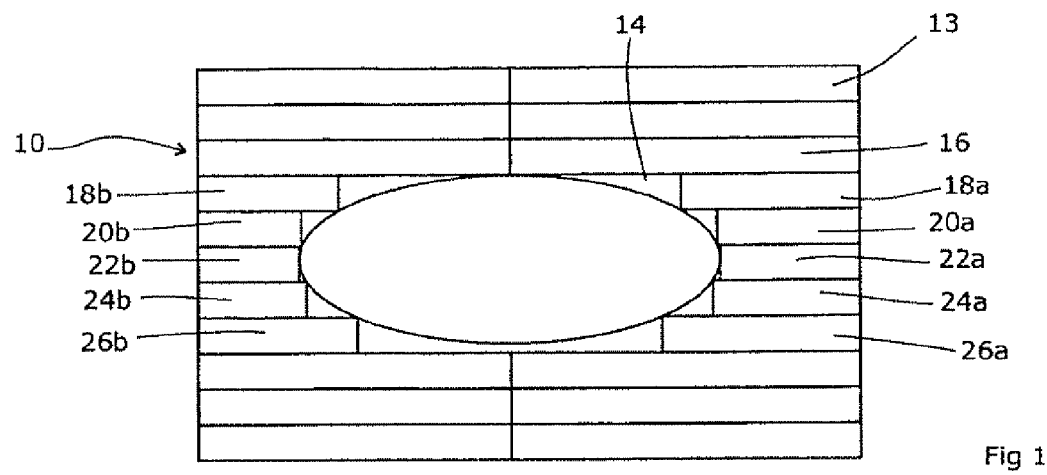
FIG. 1 shows a known multi-leaf collimator.

Referring to FIG. 1, a known form of multi-leaf collimator 10 is used to delimit a radiation beam intended to treat a tumour 12. Viewed along the axis of the radiation beam as in FIG. 1, the multi-leaf collimator 10 consists of a plurality of leaves 13 which are generally deep in the direction of the beam, elongate in a longitudinal direction transverse to the beam, and narrow in a lateral direction perpendicular to the beam. They are then arranged in an array alongside each other with their lateral faces closely adjacent and parallel. They are mounted in a support (not shown in FIG. 1) which allows individual leaves to be extended or retracted so as to define a shape 14 which generally matches the exterior of the tumour 12 as viewed along that axis. Some of the leaves such as leaf 16 are extended fully to the middle of the field, whereas adjacent leaves 18a, 20a, 22a, 24a and 26a are partially retracted so as to expose the tumour 12 to radiation. A corresponding situation exists for the leaves 18b, 20b, 22b, 24b and 26a on the opposite side of the field.

Modern advances in radiotherapy apparatus include the provision of an apparatus which combines a therapeutic treatment source with a diagnostic source and a flat panel imager for the diagnostic source. Generally a therapeutic source is mounted so as to be rotatable around the patient through 360° or more, to allow the tumour to be irradiated from a plurality of directions thereby reducing the dose to surrounding healthy tissue. Typically, the diagnostic source and the flat panel images are mounted on the same rotatable support and are usually spaced apart from the therapeutic source by 90° or thereabouts, so that they rotate around the patient together with the source and allow a three dimensional computed tomography (CT) scan to be prepared.

Figure 2:
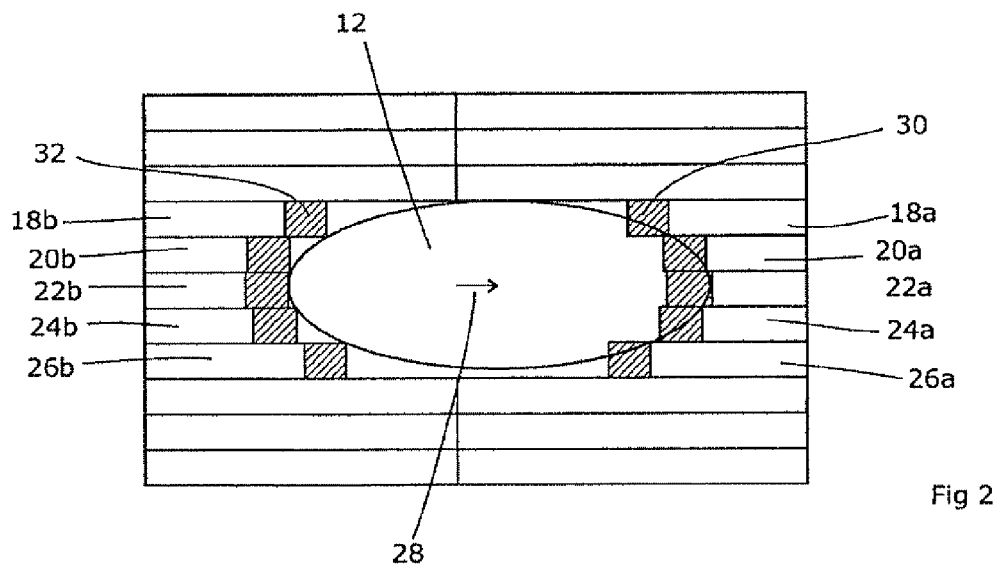
FIG. 2 shows the effect of a longitudinal movement of the target volume within such a multi-leaf collimator.

This scan and/or the underlying images, can reveal changes in the current position of the tumour, and it has been proposed that the MLC should be adjusted so as to take account of those changes. FIG. 2 shows the process of doing so. It assumes that the tumour 12 has moved a short distance 28 in a direction parallel to the longitudinal direction of the leaves. This therefore requires that the already partially retracted leaves 18a, 20a, 22a, 24a and 26a are each retracted by a further amount, shown as the shaded area 30 in FIG. 2. Likewise, the corresponding leaves 18b, 20b, 22b, 24b and 26b on the other side of the field need to be extended by a corresponding extent 32 also shown shaded in FIG. 2.

Figure 3:
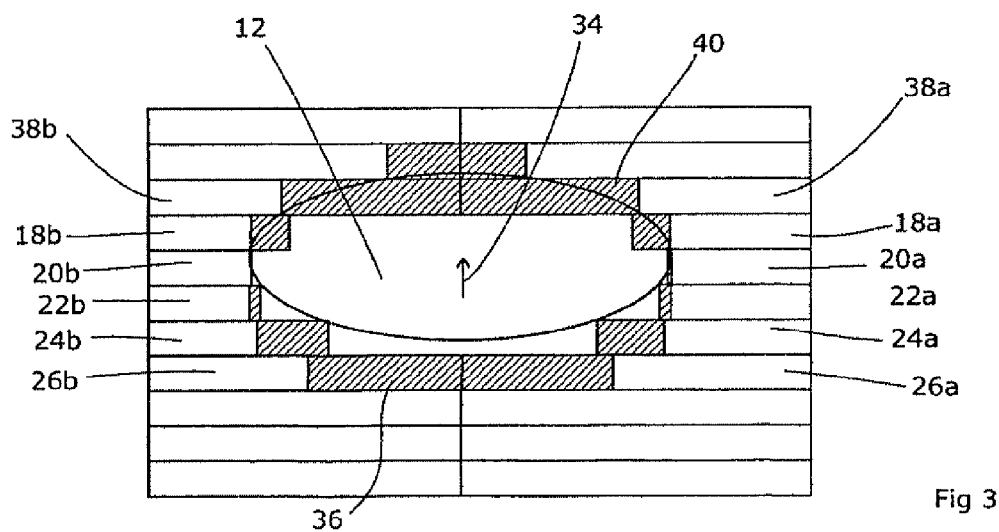
FIG. 3 shows the effect of a lateral movement in such a multi-leaf collimator.

Such adjustment of the MLC leaves is useful and straight forward where the motion is parallel or substantially parallel to the longitudinal direction of the leaves, therefore. FIG. 3 shows a difficulty which arises if the directional motion 34 is in a direction transverse to the longitudinal direction of the leaves, i.e. in a lateral direction with respect to the leaves. This means that the leaf pair 26a, 26b that were previously partially retracted now no longer cover any part of the tumour 12, and must be fully extended so as to close off the radiation field in this area. Accordingly, the movement 36 that is involved is substantial. Likewise, on the other side of the radiation field, one or more new leaf pairs 38a, 38b must be moved from a fully extended position to a largely retracted position, covering a significant distance 40, shown hatched in FIG. 3.

These movements, i.e. the additional extension 36 and the substantial retraction 40 are not minor adjustments to the leaf positions, but are significant traverses across a large proportion of the MLC field. Generally, the leaves of an MLC can only move at a pre-defined maximum speed due to the engineering constraints involved in moving a long, thin and heavy item in a confined area to a high degree of accuracy and without causing any mechanical damage such as buckling. Accordingly, the significant leaf motions 36, 40 that are required to accommodate lateral movement of the tumour 12 are likely to take a significant time relative to the speed of movement of the tumour 12. If that movement is periodic, for example as caused by respiration, then there is a distinct possibility that the motion of the tumour 12 and the adjustment of the leaves could become out of phase. In any case, there will be a significant and undesirable lag.

Figure 4:
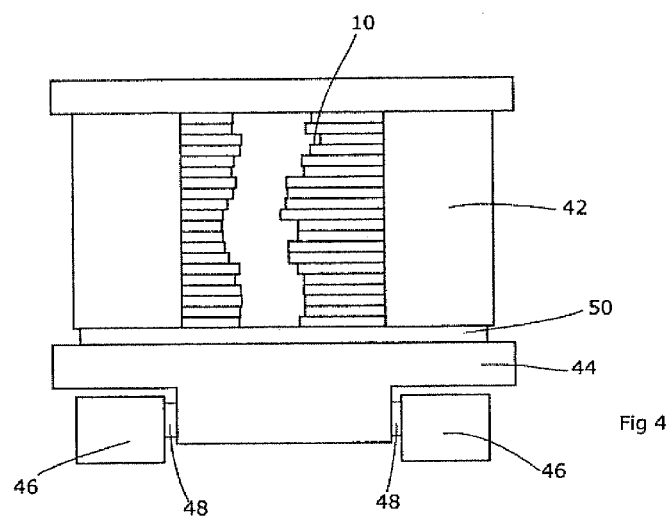
FIG. 4 shows a multi-leaf collimator according to the present invention, viewed along the beam axis.

FIG. 4 shows an embodiment of the present invention in which the leaves of the MLC 10 are mounted on a support 42 which contains the necessary positional adjustment motors (etc.). This is mounted on a support 44 which is mounted to a fixed frame 46 that is an integral part of the radiotherapy apparatus. A small adjustment mechanism 48 is provided between the support 44 and the fixed frame 46 to allow factory adjustment of the MLC default position.

Between the MLC carriage 42 and the support 44, there are a set of bearings 50 which allow the carriage 42 to move relative to the support 44 in a direction that is transverse relative to the leaves of the MLC 10. Thus, the motion of a tumour 12 that is longitudinal with respect of the leaves, as shown in FIG. 2, can be accommodated by adjustment of the leaf positions. Motion of the tumour 12 that is transverse or lateral with respect to the leaves of the MLC 10 such as shown in FIG. 3 can be accommodated by a lateral movement of the entire carriage 42 (including the leaf set). Accordingly, the leaves move sideways with the tumour 12 and the excessive leaf motions 36, 40 shown in FIG. 3 no longer required.

Figure 5:
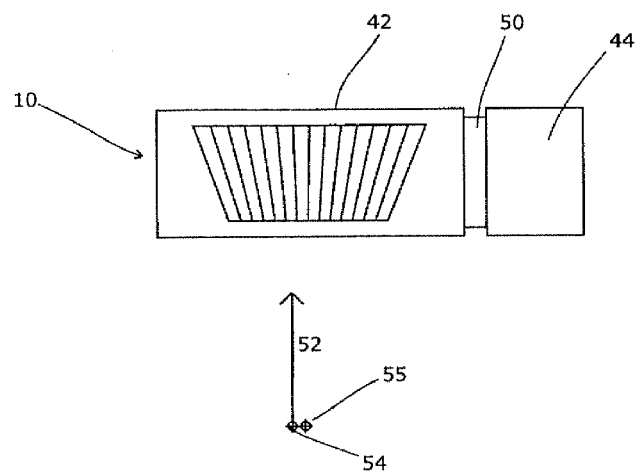
FIG. 5 shows the multi-leaf collimator of FIG. 4, viewed in section along the beam axis.
Figure 6:
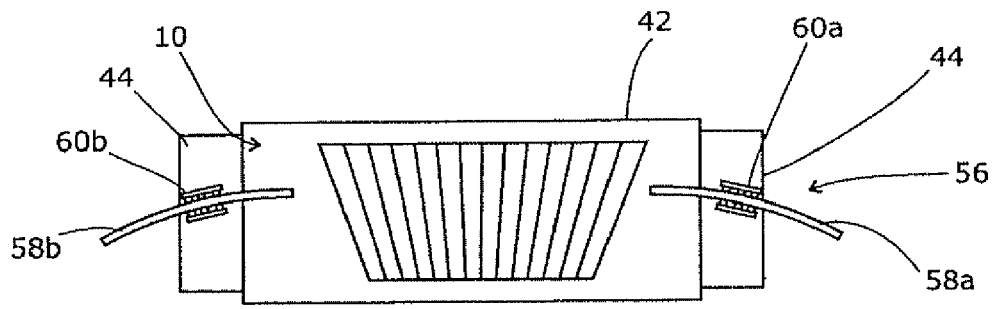
FIG. 6 shows a first possibility for controlling movement of the multi-leaf collimator.

FIG. 5 shows an MLC 10 from one side, in the plane including the beam direction 52. It can be seen that the leaves of the MLC 10 are arranged in a convergent manner, focused on a location 55 that is to one side of the source 54—i.e. the point 54 on the beam axis 52 from which the radiation can be considered to emanate. This is useful in order to minimise the radiation leakage through the gap between the leaves. An alternative approach is to provide the leaves with nesting stepped sides, or interlocking 'tongue and groove' designs. FIG. 6 therefore shows in schematic form a preferred form of bearing 50. In order to (substantially) maintain the orientation of the leaves with respect to the source 54 (not shown in FIG. 6), the carriage 42 moves relative to the support 44 on a path that is an arc centred on the source 54. Accordingly, there will be a degree of tilting of the support as it moves.

In this example, the bearing set 56 consists of a pair of arcuate guides 58a, 58b on which are mounted a respective pair of suitable roller bearings 60a, 60b that are able to move along the arcuate guides 58a, 58b. The guides 58a, 58b are attached to the surrounding support 44, and the carriage 42 is mounted on the roller bearings 60a, 60b. This mounting arrangement may be reversed if desired. The arc taken up by each of the guides 58a, 58b is a circle centred on the beam source 54. Thus, as the bearing set 56 translates the MLC 10, the individual leaves remain focused on the beam source 54.

Figures 7, 8:
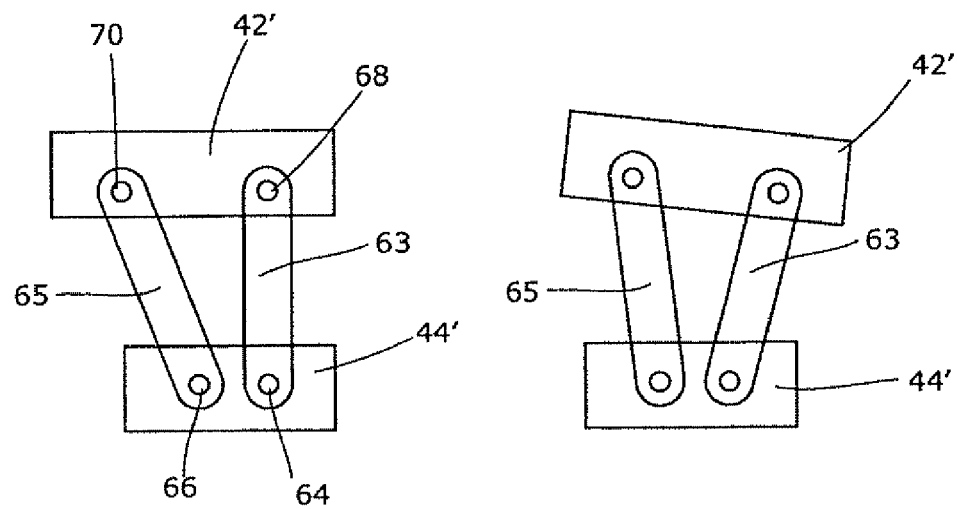
FIGS. 7 and 8 show a second possibility for controlling movement of the multi-leaf collimator.

FIGS. 7 and 8 show an alternative arrangement for the bearings 50. A fixed member 44' is attached to the support 44, and is connected to the floating member 42' attached to the carriage 42 via a pair of non-equal length pivot arms 63, 65.

Each pivot arm 63, 65 is pivoted at one end 64, 66 to the fixed member 44' and at the other end 68, 70 to the floating member 42'. As shown in FIG. 7, the spacings between the pivot 64 and 66 differs from the spacing between the pivot 68, 70 at the other end of the pivot arms 63, 65. Basic geometrical principles then dictate that the floating member 42' will move relative to the fixed member 44' along the required path; the fixing points 64, 66, 68, 70 and the lengths of the pivot arms 63, 65 can be adjusted to control that path as desired. FIG. 8 shows the position of the items after a small rotation, showing that the angle of the floating member 42' changes slightly as it moves to one side.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A radiotherapy apparatus comprising a source adapted to emit a beam of therapeutic radiation toward a target volume, a collimator for delimiting the radiation beam, and a control means, the collimator comprising a plurality of leaves arranged alongside each other and moveable longitudinally so that the tips of the leaves define a variable edge of the collimator, the leaves being mounted on a support that is moveable relative to the source in a direction that is lateral with respect to the leaves, wherein the control means is adapted to receive information as to the location of the target volume, and, on the basis of that information, control the longitudinal positions of the leaves and the lateral position of the support.

2. The radiotherapy apparatus according to claim 1 in which the support is constrained to tilt relative to the lateral motion as it moves.

3. The radiotherapy apparatus according to claim 1 in which the support is moveable laterally along a straight path.

4. The radiotherapy apparatus according to claim 1 in which the leaves within a multi-leaf collimator are non-parallel.

5. The radiotherapy apparatus according to claim 3 in which the leaves are each aligned so that they converge.

6. The radiotherapy apparatus according to claim 4 in which the leaves converge on a point offset from the source.

7. The radiotherapy apparatus according to claim 1 in which the support is constrained by being mounted on bearings that are moveable on guides.

8. The radiotherapy apparatus according to claim 1 in which the support is constrained by being mounted on a plurality of pivot arms of unequal lengths.

9. The radiotherapy apparatus according to claim 2 in which the support is moveable laterally along a straight path.

10. The radiotherapy apparatus according to claim 2 in which the leaves within a multi-leaf collimator are non-parallel.

11. The radiotherapy apparatus according to claim 3 in which the leaves within a multi-leaf collimator are non-parallel.

12. The radiotherapy apparatus according to claim 2 in which the support is constrained by being mounted on bearings that are moveable on guides.

13. The radiotherapy apparatus according to claim 3 in which the support is constrained by being mounted on bearings that are moveable on guides.

14. The radiotherapy apparatus according to claim 4 in which the support is constrained by being mounted on bearings that are moveable on guides.

15. The radiotherapy apparatus according to claim 6 in which the support is constrained by being mounted on bearings that are moveable on guides.

16. The radiotherapy apparatus according to claim 2 in which the support is constrained by being mounted on a plurality of pivot arms of unequal lengths.

17. The radiotherapy apparatus according to claim 3 in which the support is constrained by being mounted on a plurality of pivot arms of unequal lengths.

18. The radiotherapy apparatus according to claim 4 in which the support is constrained by being mounted on a plurality of pivot arms of unequal lengths.

19. The radiotherapy apparatus according to claim 6 in which the support is constrained by being mounted on a plurality of pivot arms of unequal lengths.

20. The radiotherapy apparatus according to claim 7 in which the support is constrained by being mounted on a plurality of pivot arms of unequal lengths.

* * * * *